(12) United States Patent
Lee

(10) Patent No.: US 11,819,363 B2
(45) Date of Patent: Nov. 21, 2023

(54) SYSTEMS AND METHODS TO IMPROVE RESOLUTION OF ULTRASOUND IMAGES WITH A NEURAL NETWORK

(71) Applicant: GE Precision Healthcare LLC, Milwaukee, WI (US)

(72) Inventor: Dongwoo Lee, Seoul (KR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 518 days.

(21) Appl. No.: 17/009,653

(22) Filed: Sep. 1, 2020

(65) Prior Publication Data

US 2022/0061816 A1    Mar. 3, 2022

(51) Int. Cl.
*A61B 8/08* (2006.01)
*A61B 8/00* (2006.01)
*G06T 3/40* (2006.01)
*G06N 3/045* (2023.01)

(52) U.S. Cl.
CPC .......... *A61B 8/5207* (2013.01); *A61B 8/4494* (2013.01); *A61B 8/461* (2013.01); *A61B 8/5215* (2013.01); *G06N 3/045* (2023.01); *G06T 3/4053* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 2015/0080725 A1* | 3/2015 | Wegner | G01S 15/8959 600/443 |
| 2020/0196984 A1* | 6/2020 | Sprung | A61B 8/483 |
| 2020/0405269 A1* | 12/2020 | Swisher | A61B 8/4444 |
| 2021/0068791 A1* | 3/2021 | Gebre | G06T 7/00 |
| 2021/0251610 A1* | 8/2021 | Stergiopoulos | G06V 10/26 |
| 2021/0338203 A1* | 11/2021 | Rouet | A61B 8/483 |
| 2022/0120928 A1* | 4/2022 | Hori | E21B 47/0025 |
| 2022/0233171 A1* | 7/2022 | Johnson | A61B 8/585 |
| 2022/0383500 A1* | 12/2022 | Galeotti | G06K 9/6272 |

OTHER PUBLICATIONS

Shujaat Khan, Jaeyoung Huh, and Jong Chul Ye, "Universal Deep Beamformer for Variable Rate Ultrasound Imaging", arXiv: 1901.01706v1 [cs.CV] Jan. 7, 2019.*

* cited by examiner

*Primary Examiner* — Jiangeng Sun

(74) *Attorney, Agent, or Firm* — McCoy Russell LLP

(57) ABSTRACT

The current disclosure provides for mapping ultrasound images to resolution mapped ultrasound images using generative neural networks, while maintaining clinical quality of the resolution mapped ultrasound image, thereby enabling a clinician to evaluate ultrasound images in a preferred resolution without loss of clinically relevant content. In one embodiment the current disclosure provides for a method comprising, acquiring a ultrasound image of an anatomical region of a subject, wherein the ultrasound image is in a first resolution, selecting a target resolution, wherein the target resolution is distinct from the first resolution, selecting a clinical quality metric, selecting a trained resolution mapping network based on the target resolution and the clinical quality metric, mapping the ultrasound image to a resolution mapped ultrasound image using the trained resolution mapping network, wherein the resolution mapped ultrasound image is in the target resolution, and displaying the resolution mapped ultrasound image via a display device.

23 Claims, 8 Drawing Sheets

SYSTEMS AND METHODS TO IMPROVE RESOLUTION OF ULTRASOUND IMAGES WITH A NEURAL NETWORK

TECHNICAL FIELD

Embodiments of the subject matter disclosed herein relate to ultrasound imaging, and more particularly, to systems and methods for enhancing elevational resolution in ultrasound images using a generative neural network.

BACKGROUND

Clinical ultrasound is an imaging modality that employs ultrasound waves to probe the internal structures of a body of a patient and produce a corresponding image. An ultrasound probe comprising a plurality of transducer elements emits ultrasonic pulses which reflect or echo, refract, or are absorbed by structures in the body. The ultrasound probe then receives reflected echoes, which are processed into an image. For example, a medical imaging device such as an ultrasound imaging device may be used to obtain images of a heart, uterus, liver, lungs and various other anatomical regions of a patient. An ultrasound beam produced by a single row array of transducer elements (e.g., a one dimensional (1D) ultrasound probe, or a single row array of a multi-row array) is focused by a lens, such that the thickness of the beam is at a minimum at a first depth corresponding to a focal point of the lens. At the first depth, an elevational resolution of an image acquired by the probe is maximized, whereby anatomical features visible at the first depth are shown in higher resolution than anatomical features visible at a second depth below or above the first depth. As a result, an ultrasound image acquired by a 1D probe has a first resolution profile characterized by a narrow region with high resolution, and regions in the near and far fields shown in progressively lower resolution as a function of a distance from the high resolution region.

Inconsistency in elevational resolution has been addressed by using probes with additional rows of transducer elements (e.g., 1.5 dimensional/1.5D or 2 dimensional/2D probes). An advantage of multi-row probes over single-row probes is that multi-row probes can display ultrasound images at high resolution over an extended range of depths, by adjusting the lenses of the probe such that each row of transducers is focused at a different depth and combining the ultrasound images acquired by each row of the probe. As a result, higher resolution images may be acquired, with positive benefits that may include a better patient experience, a more accurate diagnosis, and/or improved clinical outcomes.

However, multi-row array probes such as 1.5 and 2D probes rely on more elements, and as a result may be more costly than 1D (single-row array) probes. Further, the additional elements of a 1.5D or 2D probe may subject the subject to higher levels of energy than a 1D probe, which in some cases may not be desired (e.g., when acquiring images of a fetus, etc.). Ultrasound operators may also have less experience using a 1.5D or 2D probe, which may result in a reduced image quality, a longer examination time, and/or an increased time and cost of training.

SUMMARY

The current disclosure at least partially addresses one or more of the above identified issues by a method comprising: acquiring a first ultrasound image having a first resolution profile; inputting the first ultrasound image to a trained neural network algorithm; and generating a second ultrasound image having a second higher resolution profile as an output of the trained neural network algorithm.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
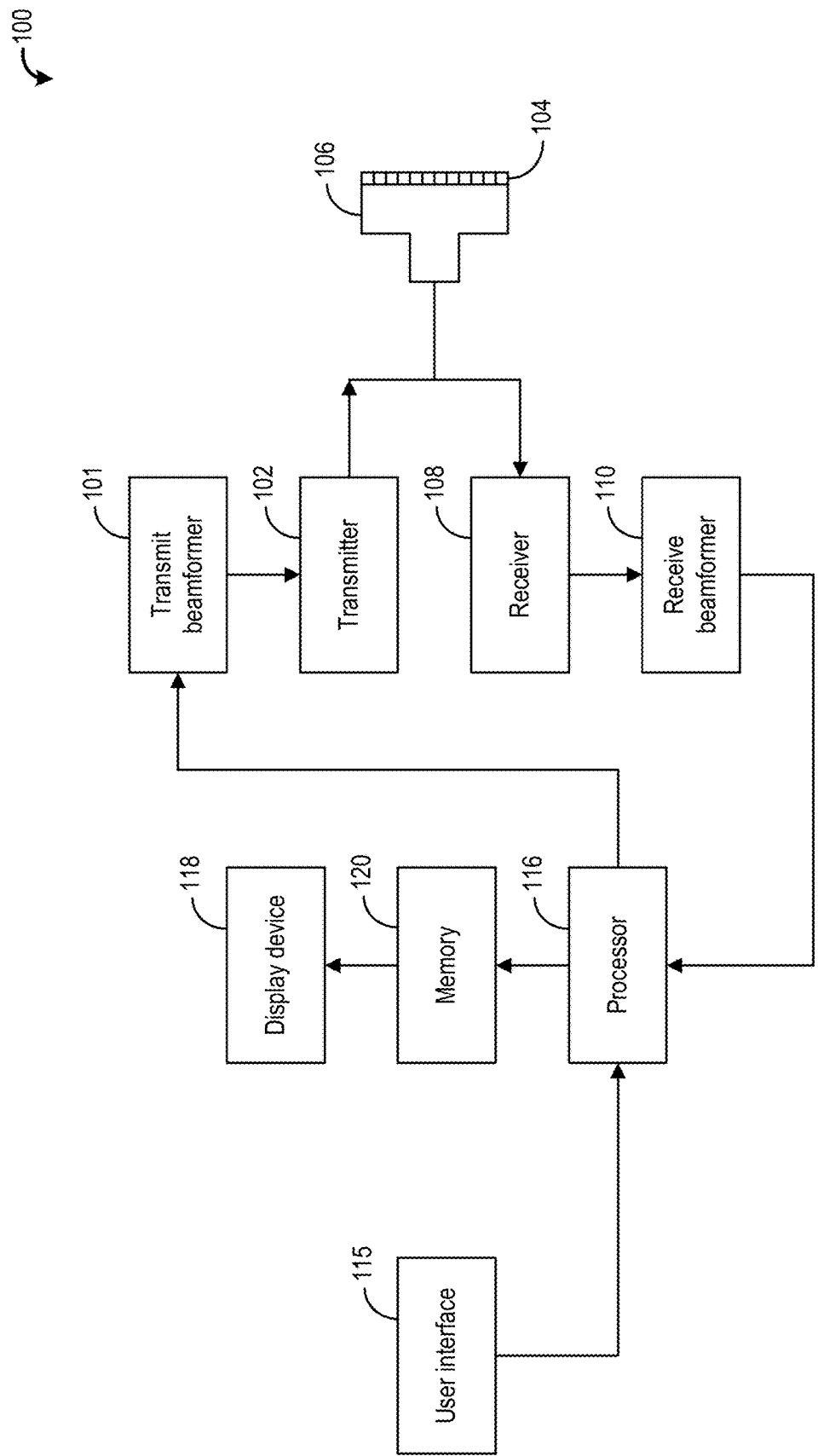
FIG. 1 shows a block diagram of an exemplary embodiment of an ultrasound system.

The drawings illustrate specific aspects of the described systems and methods for mapping one or more ultrasound images in a first resolution to one or more corresponding ultrasound images in a target resolution using generative neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

Clinical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position, pressure, and/or orientation of the ultrasound probe in order to obtain high-quality images of the target anatomical feature (e.g., the heart, the liver, the kidney, or another anatomical feature). The acquisition parameters that may be adjusted include transmit frequency, transmit depth, gain (e.g., overall gain and/or time gain compensation), cross-beam, beam steering angle, beamforming strategy, frame averaging, and/or other parameters.

The ultrasound probe may include a single-row array of transducer elements (herein, a linear array probe or 1D probe), which generates an ultrasound beam with a resolution that is defined in three dimensions. An axial resolution of the beam describes a discernibility between two points parallel to a path of the beam. A lateral resolution of the beam describes a discernibility between two points perpendicular to a path of the beam and parallel to a transducer array of the probe. An elevational resolution of the beam describes a discernibility between two points perpendicular to the transducer array of the probe at a fixed axial distance from the probe.

The ultrasound beam is typically focused by a lens, whereby the thickness of the beam varies as a function of distance from the probe, such that an initial thickness of the beam when it leaves the probe is reduced until reaching a minimum thickness at a focal point of the lens, after which point the thickness of the beam increases with the beam's distance from the probe. The focal point of the lens is at a fixed distance from the probe (e.g., a fixed depth into the body of a subject). At the fixed distance, the maximum elevational resolution of the beam is achieved. While a single row array of a 1D probe shows good elevational resolution at the focal point of the lens, elevational resolution is poor in the near and far field. For example, two points of an image that are close together in the elevational plane may be discernable at the focal point of the beam, but not discernable at a depth above or below the focal point of the beam.

Poor near and far-field elevational resolution may be addressed by using a multi-row array of transducer elements (herein, a 1.5D probe or a 2D probe), where each row of transducer elements is focused at a different focal point (e.g., a different distance from the probe or depth). The images produced by each row of transducers may be combined to create a single ultrasound image with high elevational resolution over a broader range of depths than the comparatively narrow range of a 1D probe. As a result, a multi-row array of a 1.5D or 2D probe provides uniform slice thickness and excellent contrast resolution over an extended imaging range.

Thus, images may be acquired via a 2D probe with a multi-row array of transducers in which features of an anatomical structure are shown in high resolution at a wider range of elevations. This may result in ultrasound images of higher quality, where anatomical features may be identified and viewed in greater clarity, which may lead to a better patient experience, a more accurate diagnosis, and/or improved clinical outcomes.

For example, in an ultrasound examination of a uterus of a pregnant woman performed using a 1D probe with a single row of transducers, ultrasound images may be acquired that show anatomical features of a fetus (e.g., ears, nose, etc.) at a first depth at which a beam produced by the single row of transducers is focused with a high resolution, while other anatomical features of the fetus (e.g., feet, genitalia, etc.) at a second depth (e.g., in the far or near field) may be shown with a lower resolution. In contrast, in an ultrasound examination of the uterus of the pregnant woman using a 2D probe with a plurality of rows of transducers, ultrasound images may be acquired that show anatomical features of the fetus at a range of depths with a high resolution. Generating high resolution views of an anatomical feature of interest across a range of depths using a 1D probe may involve adjusting a position of the probe over time to sweep the focal point of the 1D probe across the range of depths at which an anatomical feature of interest is visible, which may negatively impact a diagnosis or a patient experience.

However, while multi-row array (e.g., 2D) probes may produce higher resolution images than single-row array (e.g., 1D) probes, multi-row array probes may not be as widely adopted by clinicians as single-row array probes due to a higher cost associated with a greater number of transducers and control elements, higher energy output, and/or lack of operator experience.

Thus, the current disclosure provides systems and methods for a transformation of an original image, having an original resolution profile, to an output ultrasound image, having a target resolution profile, where the target resolution profile may include a high resolution over a broader range of depths than the original resolution profile. For example, the original resolution profile may be characterized as narrow, providing high resolution at a first depth but poor resolution at a second depth in the near or far field, while the target resolution profile may be characterized as broad, including high resolution across a wide range of depths in the near and far field. In one embodiment, the original image may be transformed to the target image using a trained resolution mapping network. The current disclosure further provides for training systems and methods enabling a resolution mapping network to be trained to learn a mapping from a first resolution profile to a target resolution profile.

In one embodiment, one or more ultrasound images are acquired via a 1D ultrasound probe of an ultrasound imaging system, such as the ultrasound imaging system 100 of FIG. 1. The ultrasound imaging system may be communicatively coupled to an image processing system, such as the image processing system 202 of FIG. 2. The image processing system may include one or more neural network models, such as generative neural network models and generative adversarial network models, stored in non-transitory memory. An exemplary generative neural network model (hereinafter generative neural network) is illustrated schematically in FIG. 4A, which may be trained and deployed to output an image with a broader resolution profile (e.g., similar to an image produced by a 2D ultrasound probe) using an ultrasound image acquired via a 1D ultrasound probe as input, as shown in FIG. 4B. The generative neural network algorithm may be trained using a resolution mapping network training system 300, shown in FIG. 3, by executing one or more operations of method 500 of FIG. 5, which comprises preparing a training data set for the resolution mapping network training system 300, and/or method 600 of FIG. 6, which comprises training the generative neural network algorithm to learn a mapping from a first resolution profile to a target resolution profile, wherein training image pairs comprising 1D probe images and corresponding ground-truth 2D probe images are used to adjust parameters of the generative neural network according to a backpropagation algorithm. The training image pairs may be generated by scanning an anatomical feature of a patient with both a 1D and 2D ultrasound probe device, discussed below with reference to method 500 of FIG. 5. Trained neural network models may be deployed by an image processing system, such as image processing system 202 of FIG. 2, to map one or more ultrasound images from the first resolution profile to the corresponding resolution-mapped ultrasound images with the target resolution profile, by executing one or more operations of method 700 of FIG. 7.

Referring now to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient clinical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and/or a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

An ultrasound scan may be performed using a 1D ultrasound probe or a 2D ultrasound probe. As mentioned above, a 1D ultrasound probe comprises a single row of transducers that provides an area of focus corresponding to a depth of the 1D probe, where portions of anatomical structures within a narrow elevation range of the focus depth are shown in high resolution (e.g., high elevation-wise resolution, or high resolution in an elevation direction, as opposed to a resolution in a lateral and/or axial direction), while portions of anatomical structures that are at elevations progressively further from the elevation of focus are shown in progressively lower resolutions (e.g., low elevation-wise resolution). In contrast, a 2D ultrasound probe comprises an array of n rows of transducers, providing n areas of focus, each area of focus corresponding to a different depth of the 2D ultrasound probe, where portions of anatomical structures within a narrow depth range from each area of focus are shown in high resolution. As a result, images acquired via a 2D probe with a multi-row array of transducers show anatomical features in high resolution across a wider range of probe elevations.

After performing an ultrasound scan, a two-dimensional block of data comprising scan lines and their samples is generated for each row of transducers comprised by the ultrasound probe (e.g., one block of data for a 1D probe, or n blocks of data for a 2D probe with n rows of transducers). After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

If a 2D probe with n rows of transducers is used to perform the ultrasound scan, n scan-converted images will be generated, where each of the n images will show a different region of the image with high resolution, such that the n scan-converted images may be combined into a single scan-converted image where anatomical features are shown in high resolution over a wider region of the image as compared with a 1D probe.

Ultrasound images acquired by ultrasound imaging system 100 may be further processed. In some embodiments, as described in greater detail below, ultrasound images produced by ultrasound imaging system 100 may be transmitted to an image processing system, where in some embodiments, the ultrasound images may be analyzed by one or more machine learning models trained using ultrasound images and corresponding ground truth images in order to improve quality issues of the ultrasound images. As used herein, ground truth output refers to an expected or "correct" output based on a given input into a machine learning model. For example, if a machine learning model is being trained to increase the resolution of relevant portions of an ultrasound image, the ground truth output for the model, when fed an input image, is an ultrasound image in which the relevant portions are shown in high resolution.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Figure 2:
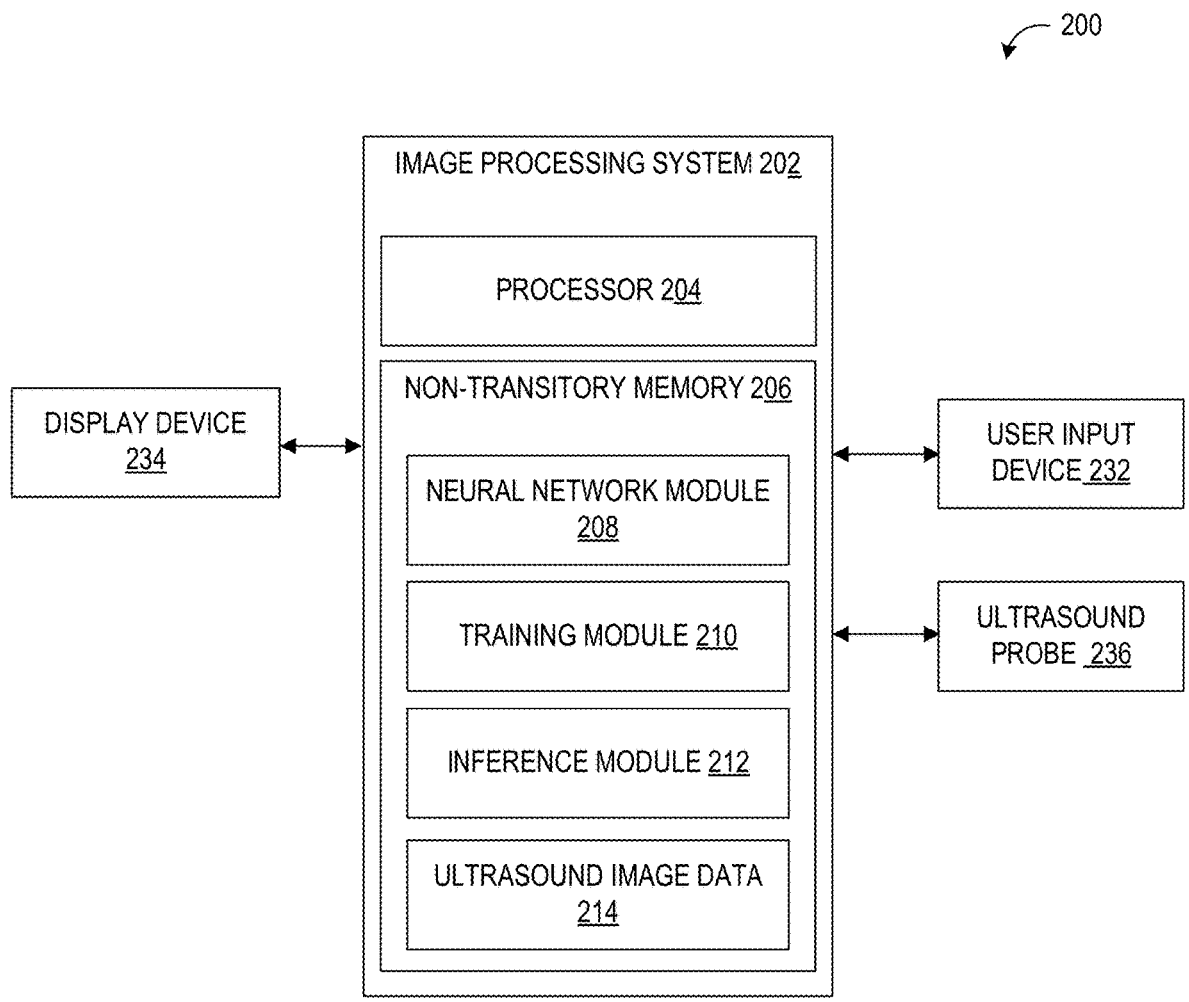
FIG. 2 shows a block diagram of an exemplary embodiment of an image processing system configured to map ultrasound images from an originating resolution profile to a target resolution profile, using a trained generative network.

Referring to FIG. 2, image processing system 202 is shown, in accordance with an embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images from the ultrasound imaging system or from a storage device which stores the images/data generated by the ultrasound imaging system. Image processing system 202 may be operably/communicatively coupled to a user input device 232 and a display device 234. The user input device 232 may comprise the user interface 115 of the ultrasound imaging system 100, while the display device 234 may comprise the display device 118 of the ultrasound imaging system 100, at least in some examples. Image processing system 202 may also be operably/communicatively coupled to an ultrasound probe 236. As discussed in further detail below, the ultrasound probe 236 may be a 1D probe, or the ultrasound probe 236 may be a 2D probe.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store a neural network module 208, a network training module 210, an inference module 212, and ultrasound image data 214. neural network module 208 may include at least a deep learning model (e.g., a generative neural network or generative adversarial network), and instructions for implementing the deep learning model to reconstruct an ultrasound image acquired via a 1D probe as an image with higher resolution in a broader range of elevations typical of a 2D probe, as described in greater detail below. Neural network module 208 may include trained and/or untrained neural networks and may further include various data, or metadata pertaining to the one or more neural networks stored therein.

Non-transitory memory 206 may further store training module 210, which comprises instructions for training one or more of the neural networks stored in neural network module 208. Training module 210 may include instructions that, when executed by the processor 204, cause image processing system 202 to conduct one or more of the steps of method 500 for a generation of a training data set, and method 600 for training the neural network model with the training data set, discussed in more detail below in reference to FIGS. 5 and 6, respectively. In some embodiments, training module 210 includes instructions for implementing one or more gradient descent algorithms, applying one or more loss functions, and/or training routines, for use in adjusting parameters of one or more neural networks of neural network module 208.

Non-transitory memory 206 also stores an inference module 212 that comprises instructions for testing new data with the trained deep learning model. The reconstruction and enhancement of ultrasound images with the trained deep learning model may be performed with the inference module 212 as described in FIG. 7. In particular, inference module 212 may include instructions that, when executed by processor 204, cause the image processing system 202 to conduct one or more of the steps of method 700, as described in further detail below.

Non-transitory memory 206 further stores ultrasound image data 214. Ultrasound image data 214 may include for example, ultrasound images acquired via a 1D ultrasound probe and images acquired via a 2D ultrasound probe. For example, the ultrasound image data 214 may store images acquired via a 1D probe and images acquired via a 2D probe of the same anatomical features of a same patient. In some embodiments, ultrasound image data 214 may include a plurality of training sets generated as discussed at method 500.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an interventional device in the ultrasound image data 214, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
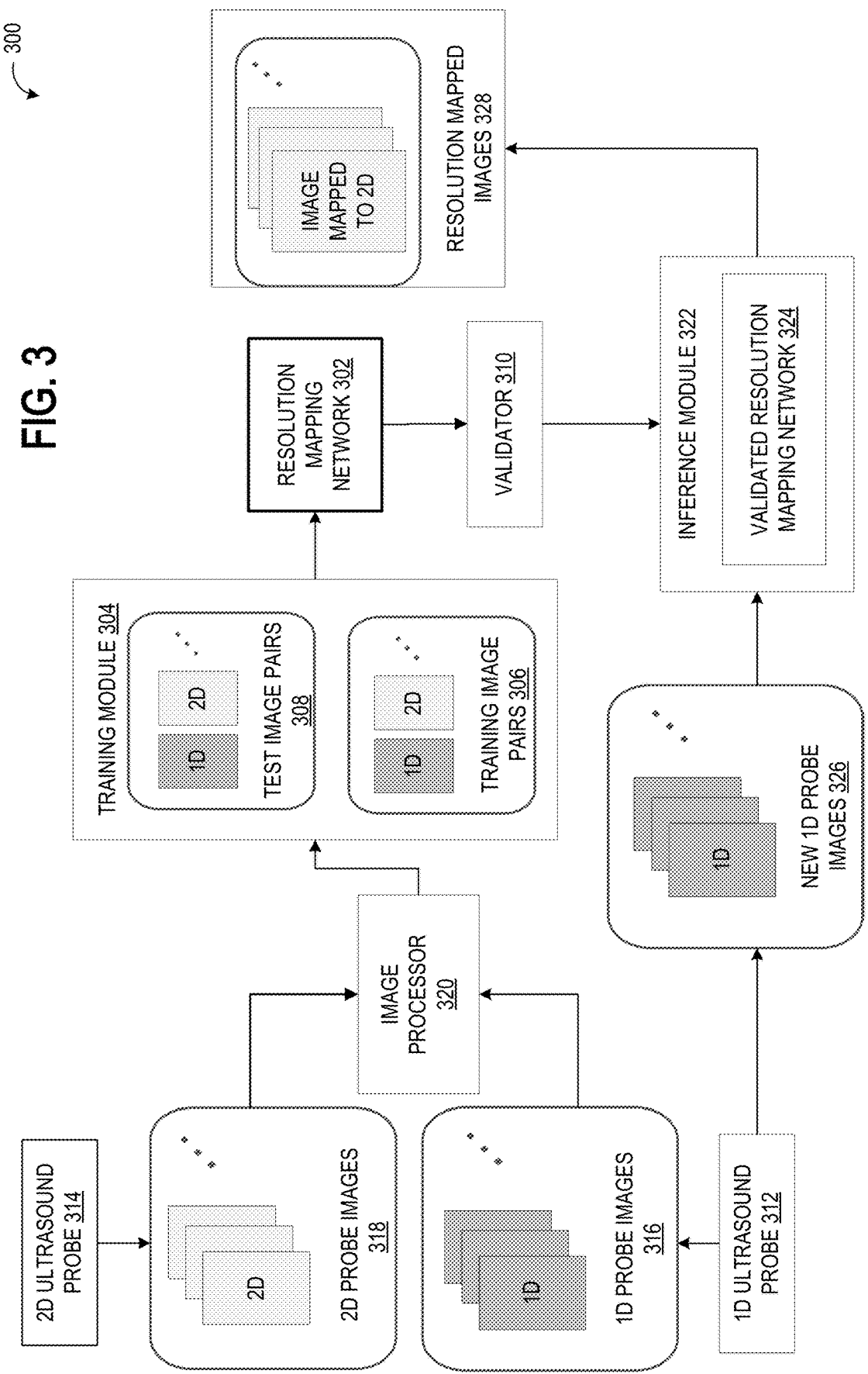
FIG. 3 shows a block diagram of an exemplary embodiment of a resolution mapping network training system.

Referring to FIG. 3, an example of a resolution mapping network training system 300 is shown. Resolution mapping network training system 300 may be implemented by one or more computing systems, such as image processing system 202 of FIG. 2, to train a resolution mapping network to learn a mapping from a first resolution profile to a target resolution profile. In an embodiment, resolution mapping network training system 300 includes a resolution mapping network 302, to be trained, and a training module 304 that includes a training dataset comprising a plurality of image pairs divided into training image pairs 306 and test image pairs 308. The training module 304 may be the same as or similar to the training module 210 of image processing system 200 of FIG. 2.

A number of training sets and a number of test sets may be selected to ensure that sufficient training data is available to prevent overfitting, whereby the resolution mapping network 302 learns to map features specific to samples of the training set that are not present in the test set. As a non-limiting example, the number of training sets used is 10,000, and the number of test sets used is 1000.

Each image pair of the training image pairs 306 and the test image pairs 308 comprises one input image and one target image, where the input image is acquired via a 1D ultrasound probe 312 of an ultrasound imaging system (e.g., the ultrasound imaging system 100 of FIG. 1) during a first examination of one or more anatomical structures of a patient, and the target image is acquired via a 2D ultrasound probe 314 of the ultrasound imaging system during a second examination of the one or more anatomical structures of the patient. In an embodiment, an ultrasound operator may perform the second examination of the patient upon completing the first examination of the patient, such that a duration of time between the first examination and the second examination is minimized, thereby ensuring that there are no changes to the anatomical structures being examined between the first examination and the second examination. Further, during the first examination a position of the 1D ultrasound probe 312 may be adjusted in order to acquire the input image via a mechanized, repeatable automatic process, whereby during the second examination a position of the 2D ultrasound probe 314 may be adjusted in order to acquire the corresponding target image via the same mechanized, repeatable automatic process. For example, during the first examination the 1D ultrasound probe may be mechanically coupled to a device such as a mechanical arm that adjusts a position of the 1D probe in one or more directions, such that when the 2D probe is mechanically coupled to the device during the second examination, a corresponding position of the 2D probe is equally adjusted in the one or more directions. Thus a high degree of correlation may be established between an input image acquired during the first examination via the 1D probe, after a fixed time interval after initiation of the first examination, and a corresponding target image acquired during the second examination via the 2D probe, after the same fixed time interval after initiation of the second examination, with respect to a position of the anatomical structure being examined. In one example, a set of ultrasound scanning parameters may be maintained between a first scan with the 1D probe and a second scan with a 2D probe. For example, the 1D probe may be adjusted to scan a first volume of an anatomical region with a first set of acquisition parameters (e.g., focus, depth, frequency, scan plane, aperture size, etc.), and subsequently the 2D probe may be adjusted to scan the same first volume with the same first set of acquisition parameters, or vice-versa. Further, in order to generate a large training data set, a plurality of anatomical regions may be scanned with the 1D probe and the 2D probe. In this way, for a training image pair, a high-correlation may be obtained between an image acquired via a 1D probe and an image acquired via a 2D probe.

Further, in some embodiments, the input image and the target image may be timestamped, whereby a first input image acquired upon initiation of the first examination is assigned a time of 0, and a first target image acquired upon initiation of the second examination is assigned a time of 0, such that any subsequent input image acquired in the first examination will be correlated with a subsequent target image acquired in the second examination that has the same timestamp. As a result, image pairs comprising 1D probe input images and 2D probe target images of the same anatomical features of the same patient may be obtained efficiently via an automated process. An example method for a process of generating training data is described in further detail below with respect to FIG. 5.

In an embodiment, the input image and the target image may be pre-processed by an image processor 320 prior to generating an image pair to be included in the training image pairs 306 or the test image pairs 308. For example, the input image may be shifted in a direction in order to adjust a position of the anatomical structure being examined with respect to a reference frame of the image acquired via a 1D probe to a position that matches a position of the anatomical structure being examined in the target image with respect to a reference frame of the image acquired via a 2D probe.

Thus, an image pair is generated comprising an input image (e.g., one of the 1D probe images 316 generated by the 1D ultrasound probe 312) and a corresponding target image (e.g., one of the 2D probe images 318 generated by the 2D ultrasound probe 314), where the target image and the input image have the same timestamp. Once the image pair is generated, the image pair may be assigned to either the training image pairs 306 dataset or the test image pairs 308 dataset. In an embodiment, the image pair may be assigned to either the training image pairs 306 dataset or the test image pairs 308 dataset randomly in a pre-established proportion. For example, the image pair may be assigned to either the training image pairs 306 dataset or the test image pairs 308 dataset randomly such that 90% of the image pairs generated are assigned to the training image pairs 306 dataset, and 10% of the image pairs generated are assigned to the test image pairs 308 dataset. Alternatively, the image pair may be assigned to either the training image pairs 306 dataset or the test image pairs 308 dataset randomly such that 85% of the image pairs generated are assigned to the training image pairs 306 dataset, and 15% of the image pairs generated are assigned to the test image pairs 308 dataset. It should be appreciated that the examples provided herein are for illustrative purposes, and image pairs may be assigned to the training image pairs 306 dataset or the test image pairs 308 dataset via a different procedure and/or in a different proportion without departing from the scope of this disclosure.

Figure 6:
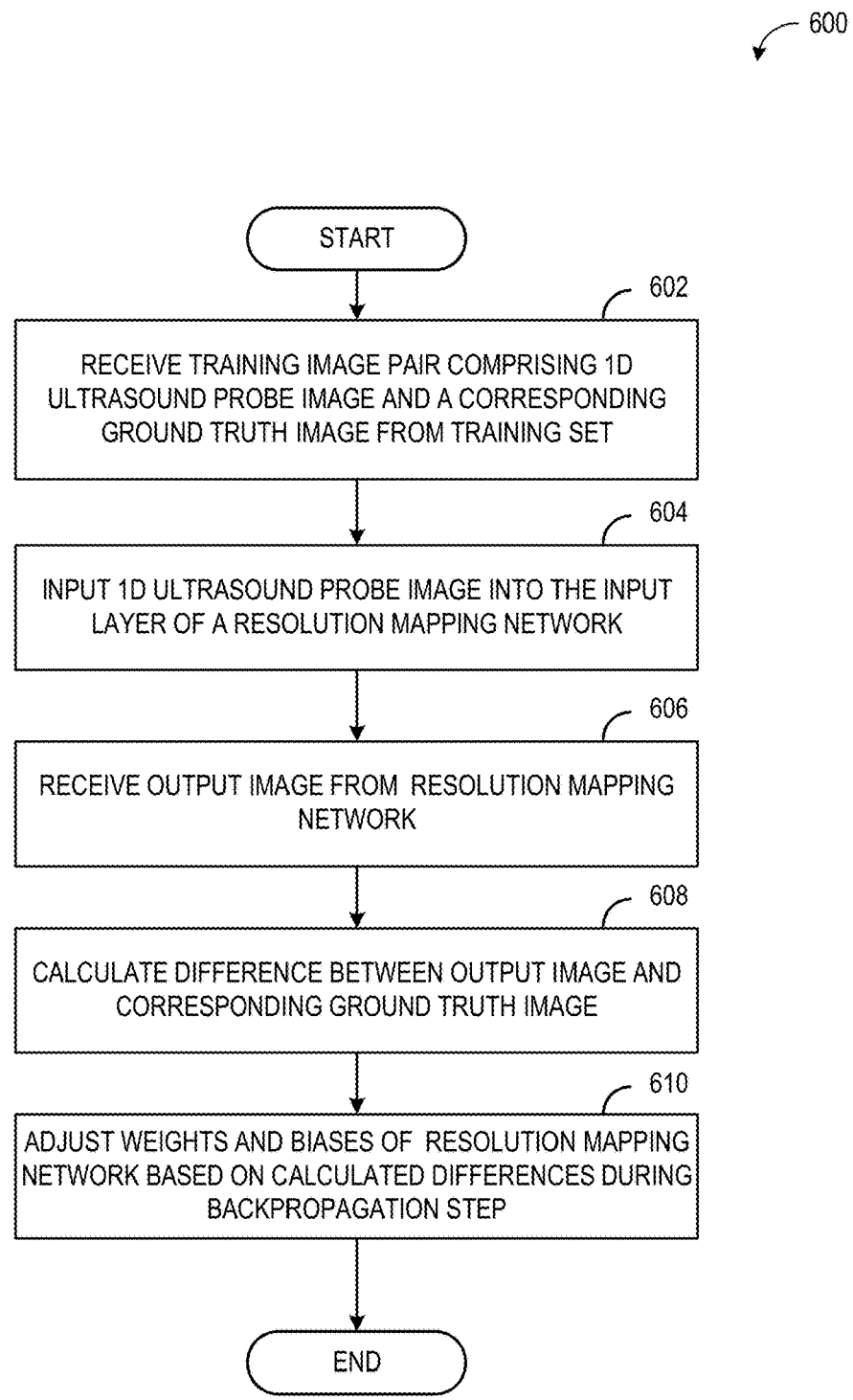
FIG. 6 shows a flowchart of an exemplary method for training a resolution mapping network using the resolution mapping network training system of FIG. 3.

Resolution mapping network training system 300 may be implemented according to one or more operations of method 600 of FIG. 6, to train the resolution mapping network 302 to learn a mapping from the resolution profile characterized by the ultrasound images 316, to the resolution profile characterized by target ultrasound images 318. Resolution mapping network 302 is configured to receive training image pairs 306 from the training module 304, and to iteratively adjust one or more parameters of the resolution mapping network 302 in order to minimize an error function based on an assessment of differences between the input image and target image comprised by each image pair of the training image pairs 306. In one embodiment, the error function may be a per-pixel loss function, where differences between the input image and the target image are compared on a pixel-by-pixel basis and summed. In another embodiment, the error may be a perceptual loss function, where features extracted from the images are compared (e.g., where loss is defined by a mean of the squared errors between all the pixels). In other embodiments, the loss function may be a minimax loss function, or a Wasserstein loss function. It should be appreciated that the examples provided herein are for illustrative purposes, and other types of loss functions may be used without departing from the scope of this disclosure.

In some embodiments, resolution mapping network 302 may comprise a generative neural network. In some embodiments, resolution mapping network 302 may comprise a generative adversarial network. In some embodiments, resolution mapping network 302 may comprise a generative neural network having a U-net architecture. In some embodiments, resolution mapping network 302 may comprise a generative neural network having a variational autoencoder architecture, comprising a first encoding portion, which compresses the information of ultrasound images 102 into a condensed representation/encoding, and a decoder portion, which decompresses the condensed representation/ encoding to a variation of the ultrasound images 102. In some embodiments, the encoding portion comprises one or more convolutional layers, which in turn comprise one or more convolutional filters (e.g., a convoluted neural network architecture). The convolutional filters may comprise a plurality of weights, wherein the values of the weights are learned during a training procedure, such as the training method of FIG. 6. The convolutional filters may correspond to one or more visual features/patterns, thereby enabling the resolution mapping network 302 to identify and extract features from the ultrasound images 316. The encoding portion may further comprise one or more down sampling operations, and/or one or more activation functions. The decoding portion may comprise one or more up-sampling, and/or deconvolution operations, which enable a compressed representation of the ultrasound images 316 to be reconstructed into an image of the same size as the ultrasound images 316.

Resolution mapping network training system 300 may include a validator 310 that validates the performance of the resolution mapping network 302 against the test image pairs 308. The validator 310 may take as input a trained or partially trained resolution mapping network 302 and a dataset of test image pairs 308, and may output an assessment of the performance of the trained or partially trained resolution mapping network 302 on the dataset of test image pairs 308. In an embodiment, the assessment of the performance of the trained or partially trained resolution mapping network 302 may be determined based on an average of a minimum error rate achieved on each image pair of test image pairs 308, where the minimum error rate is a function of one or more differences between an image outputted by the trained or partially trained resolution mapping network 302 as result of an input image of the image pair and a target ultrasound image of the image pair. In another embodiment, the assessment of the performance of the trained or partially trained resolution mapping network 302 may include a quality assessment of an ultrasound image outputted by the trained or partially trained resolution mapping network 302, where the quality assessment is determined by one or more pre-established, objective variables such as a lateral, axial, and/or elevational resolution of an output image in comparison with a target image. In other embodiments, the assessment of the performance of the trained or partially trained resolution mapping network 302 may include a combination of an average minimum error rate and a quality assessment, or a different function of the minimum error rates achieved on each image pair of the test image pairs 308 and/or one or more quality assessments, or another factor for assessing the performance of the trained or partially trained resolution mapping network 302. It should be appreciated that the examples provided herein are for illustrative purposes, and other error functions, error rates, quality assessments, or performance assessments may be included without departing from the scope of this disclosure.

For example, a partially trained resolution mapping network 302 may be validated with a test dataset of 50 image pairs 308, where each of the 50 image pairs 308 comprises an input image of a spleen of a subject acquired via a 1D ultrasound probe, and a target image of the spleen acquired via a 2D ultrasound probe adjusted to the same position on the subject as the 1D ultrasound probe. The input image acquired via the 1D ultrasound probe may have a first elevational resolution profile characterized by a narrow region of high resolution, and the target image acquired via the 2D ultrasound probe may have a second elevational resolution profile characterized by a broad region of high resolution. The validator 310 may feed the input image into the partially trained resolution mapping network 302 and receive an output image comprising a reconstruction of the input image with an expanded resolution profile (e.g., an elevational resolution profile where the output image has a larger region of high resolution than the region of high resolution of the input image). The validator 310 may then compare the output image of the spleen generated by the partially trained resolution mapping network 302 with the target image of the spleen from the relevant image pair, and output a value indicating a degree of similarity between the output image and the target image. The degree of similarity may be determined by a comparison of one or more measurements between anatomical features identified in both images, or differences in contrast between the images or portions of the images, or another similar metric. In an embodiment, the degree of similarity may be expressed as a percentage (e.g., a 90% similarity rating), and the validator 310 may return a binary result of 1 indicating that the degree of similarity exceeds a threshold similarity percentage (e.g., 85%), and that the partially trained resolution mapping network 302 has successfully mapped the input image with the first resolution profile to an image (e.g., the output image) with the second resolution profile. Alternatively, the validator 310 may return a binary result of 0 indicating that the degree of similarity does not exceed a threshold similarity percentage (e.g., 95%), and that the partially trained resolution mapping network 302 has failed to successfully map the input image with the first resolution profile to an image (e.g., the output image) with the second resolution profile. The validator 310 may validate the partially trained resolution mapping network 302 on each image pair of the test image pairs 308, and average the results of the similarity assessments performed for each image pair of the test image pairs 308 to determine an overall validation score. If the overall validation score exceeds a threshold (e.g. 0.8), the partially trained resolution mapping network 302 is thereby validated, whereby the resolution mapping network 302 has been fully trained and may be used to map new ultrasound images acquired by the 1D probe to resolution-mapped images with an extended elevational resolution profile. Alternatively, if the overall validation score does not exceed a threshold (e.g. 0.8), the partially trained resolution mapping network 302 is invalidated, indicating that the resolution mapping network 302 may not be used to map new ultrasound images acquired by the 1D probe to resolution-mapped images with an extended elevational resolution profile. In other embodiments, the validator 310 may output a similarity rating or percentage instead of a binary value, and the similarity ratings or percentages for each image pair may be averaged to determine an overall validation score. It should be appreciated that the examples provided herein are for illustrative purposes, and other procedures and/or functions may be used to validate a performance of a partially trained resolution mapping network 302 without departing from the scope of this disclosure.

Resolution mapping network training system 300 may include an inference module 322, which comprises a validated resolution mapping network 324 that has been validated by the validator 310 as described above. The inference module 322 may also include instructions for deploying the validated resolution mapping network 324 to generate a set of resolution-mapped images 328 from a set of new 1D probe images 326. The resolution mapped ultrasound images 328 may comprise a same number of images as the new 1D probe images 326, wherein for each image of the new 1D probe images 326, a corresponding resolution mapped ultrasound image 328 is produced, such that there is a 1-to-1 correspondence between the new 1D probe images 326 and resolution mapped ultrasound images 328. In this way, resolution mapping network training system 300 enables a resolution mapping network 302 to learn a map from a first resolution profile, to a target resolution profile.

Figure 4A:
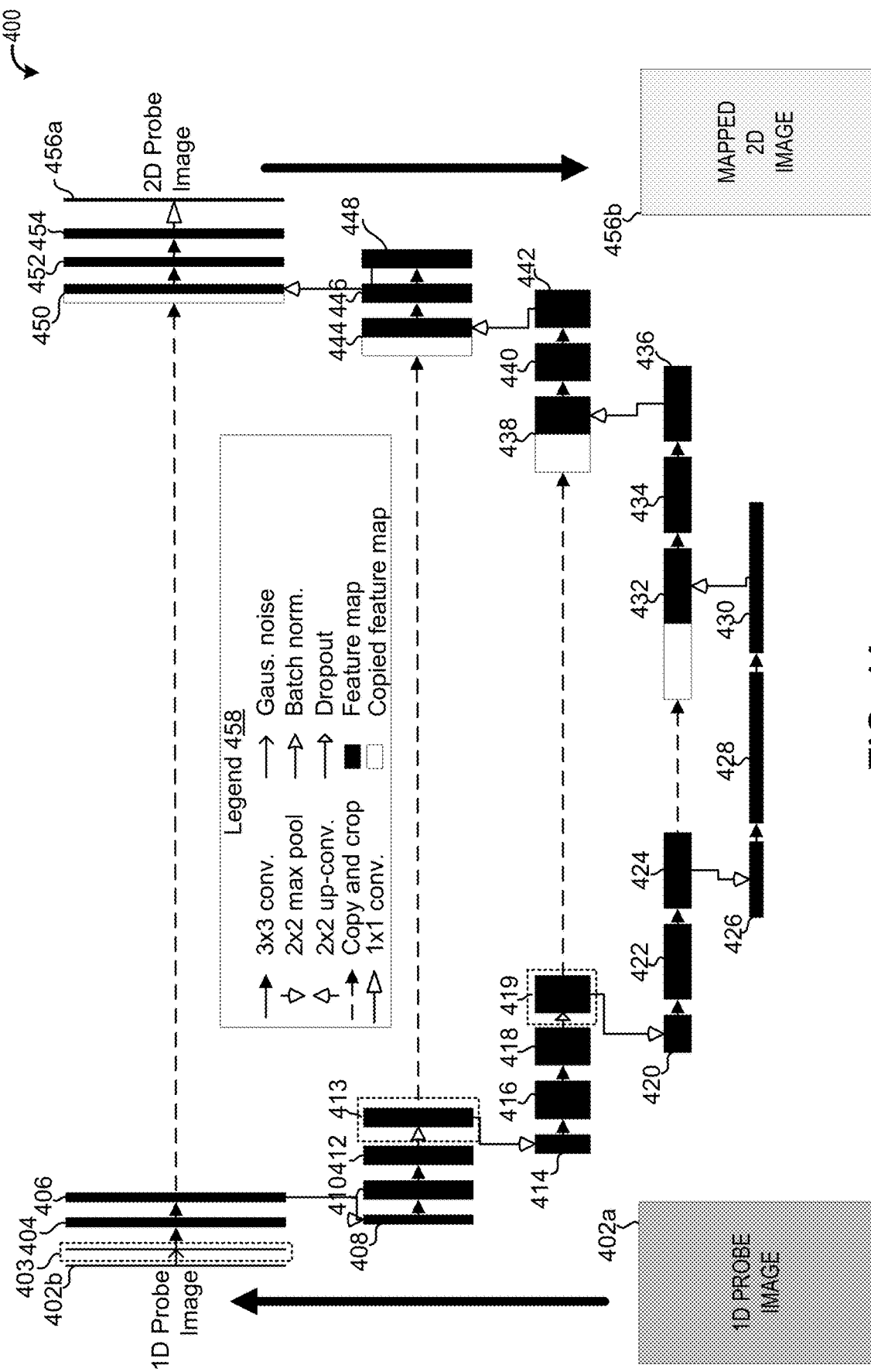
FIG. 4A is an architecture diagram of an exemplary generative neural network which may be used in the system of FIG. 3, according to an exemplary embodiment.
Figure 4B:
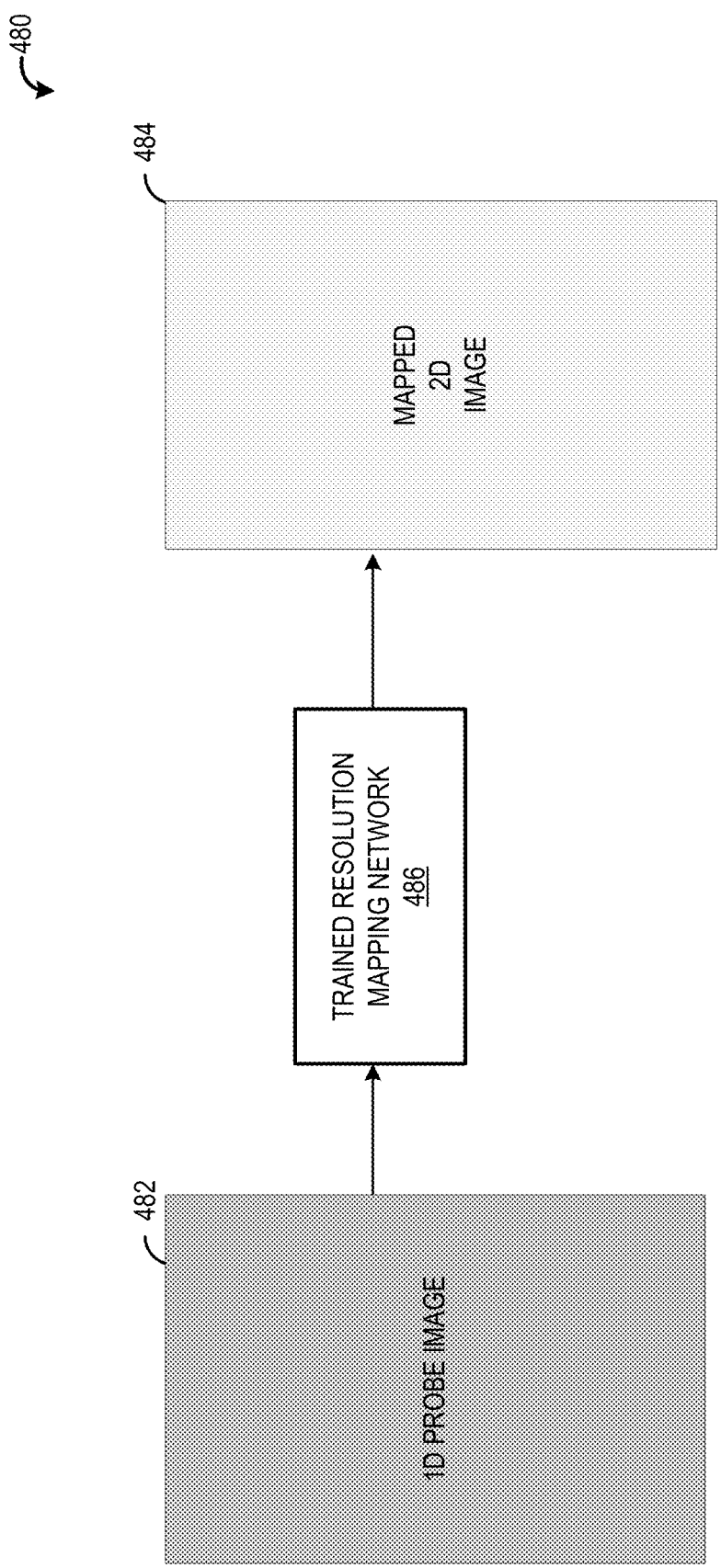
FIG. 4B shows an example input image and an example output image of a trained resolution mapping network.

Turning to FIG. 4A, an architecture diagram of CNN 400 is shown. CNN 400 may take as input two dimensional ultrasound images acquired via a 1D ultrasound probe, and generate as output two dimensional ultrasound images with a broader resolution profile, similar to images acquired via a 2D ultrasound probe. CNN 400 represents a U-net architecture, which may be divided into an encoding portion (descending portion, elements 402b-430) and a decoding portion (ascending portion, elements 432-456a). CNN architecture 400 includes a series of mappings, from a pixel representation of an input image 402b which may be received by an input layer, through a plurality of feature maps, and finally to a pixel representation of an output image 456b, which may be produced by an output layer 456a.

The various elements comprising CNN architecture 400 are labeled in legend 458. As indicated by legend 458, CNN architecture 400 includes a plurality of feature maps (and/or copied feature maps), wherein each feature map may receive input from a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length and width (which may correspond to features of each pixel of the input image) wherein the dimensions refer to the number of neurons comprising the feature map (e.g., the number of neurons along a length and the number of neurons along a width of a specified feature map).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN.

The transformations/mappings performed by each feature map are indicated by arrows, wherein each type of arrow corresponds to a distinct transformation, as indicated by legend 458. Rightward pointing solid black arrows indicate 3×3 convolutions with stride of one, wherein output from a 3×3 grid of feature channels of an immediately preceding feature map are mapped to a single feature channel of a current feature map. Each 3×3 convolution may be followed by an activation function, wherein, in one embodiment, the activation function comprises a rectified linear unit (ReLU).

Downward pointing hollow arrows indicate 2×2 max pooling, wherein the max value from a 2×2 grid of feature channels is propagated from an immediately preceding feature map to a single feature channel of a current feature map, thereby resulting in an 8-fold reduction in spatial resolution of the immediately preceding feature map. In some examples, this pooling occurs for each feature independently.

Upward pointing hollow arrows indicate 2×2 up-convolutions, which comprise mapping output from a single feature channel of an immediately preceding feature map to a 2×2 grid of feature channels in a current feature map, thereby increasing the spatial resolution of the immediately preceding feature map 8-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map are equal, no cropping may be performed.

Rightward pointing arrows with hollow elongated triangular heads indicate a 1 x1 convolution, in which each feature channel in an immediately preceding feature map is mapped to a single feature channel of a current feature map, or in other words, wherein a 1-to-1 mapping of feature channels between an immediately preceding feature map and a current feature map occurs.

Rightward pointing arrows with chevron heads indicate incorporation of Gaussian noise into a received input feature map.

Rightward pointing arrows with arcuate hollow heads indicate batch normalization operations, wherein a distribution of activations of an input feature map are normalized.

Rightward pointing arrows with a short hollow triangular head indicates a dropout operation, wherein random or pseudo-random dropout of input neurons (as well as their inputs and outputs) occurs during training.

In addition to the operations indicated by the arrows within legend 458, CNN architecture 400 includes solid filled rectangles corresponding to feature maps, wherein feature maps comprise a height (top to bottom length as shown in FIG. 4A, corresponding to a y spatial dimension in an x-y plane), width (not shown in FIG. 4A, assumed equal in magnitude to height, corresponding to an x spatial dimension in an x-y plane), and depth (a left-right length as shown in FIG. 4A, corresponding to the number of features within each feature channel). Likewise, CNN architecture 400 includes hollow (unfilled) rectangles, corresponding to copied and cropped feature maps, wherein copied feature maps comprise height (top to bottom length as shown in FIG. 4A, corresponding to a y spatial dimension in an x-y plane), width (not shown in FIG. 4A, assumed equal in magnitude to height, corresponding to an x spatial dimension in an x-y plane), and depth (a length from a left side to a right side as shown in FIG. 4A, corresponding to the number of features within each feature channel).

Starting at input image volume 402b (herein also referred to as an input layer), data corresponding to an image from a 1D ultrasound probe, such as that shown by input image 402a, may be input and mapped to a first set of features. In some embodiments, the input data is acquired by scanning target anatomical features of a patient with a 1D ultrasound probe, in accordance with method 500 of FIG. 5.

Output layer 456a may comprise an output layer of neurons, wherein each neuron may correspond to a pixel of an output ultrasound image, and wherein output of each neuron may correspond to a predicted anatomical feature (or lack of the anatomical feature) in a given location within the input ultrasound image. For example, the output of a neuron may indicate whether the corresponding pixel of the output ultrasound image is part of a spleen or is not part of a spleen. As shown in FIG. 4A, the output image 456b may illustrate one or more features included in the input image 402a.

In this way, CNN architecture 400 may enable mapping of an input ultrasound image to a predicted ultrasound image with a wider range of regions of high resolution. CNN architecture 400 illustrates the feature map transformations which occur as an input image volume is propagated through the neuron layers of the convolutional neural network, to produce the predicted output image.

The weights (and biases) of the convolutional layers in CNN 400 are learned during training, as will be discussed in more detail with reference to FIG. 6 below. Briefly, a loss function is defined to reflect the difference between the output image predicted by the CNN 400 and a corresponding ground-truth ultrasound image acquired via a 2D ultrasound probe. For example, the loss function may be a perceptual loss function, wherein a comprehensive introduction of perceptual loss may be used to control the appearance of artifacts. The loss may be back-propagated through the layers of the neural network to update the weights (and biases) of the convolutional layers. A plurality of training image pairs, comprising ultrasound images acquired from an examination of a patient using a 1D probe and corresponding ground-truth images acquired from an examination of a patient using a 2D probe, may be used to train the neural network 400.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 4A, or may replace one or more of the shown layers/feature maps.

It should be understood that the architecture and configuration of CNN 400 shown in FIG. 4A is for illustration, not for limitation, and other appropriate neural networks may be used herein for predicting ultrasound images with an extended range of high resolution areas from ultrasound images with a more limited range of high resolution areas, such as ResNet, recurrent neural networks, General Regression Neural Network (GRNN), etc.

Referring to FIG. 4B, an example is shown of an input image 482, with a first resolution profile, being mapped to a resolution-mapped ultrasound image 484, with a second resolution profile, by a trained resolution mapping network 486. The trained resolution mapping network 486 may be the same as or similar to the validated resolution mapping network 324 of FIG. 3. Input image 482 may comprise an ultrasound image acquired by an ultrasound imaging system such as the ultrasound imaging system 100 of FIG. 1. Images acquired by the ultrasound imaging system may not meet a clinician's image appearance preferences, and in response, the clinician may employ a method, such as method 700, to map the input ultrasound image 482 to a resolution mapped ultrasound image 484, wherein the resolution mapped ultrasound image 484 meets the preferences of the clinician with respect to a resolution of the image in the near field and far field. (e.g., that the resolution profile of the resolution-mapped ultrasound image 484 matches a target resolution profile defining the image appearance preferred by the clinician). Thus, both the input ultrasound image 482 and resolution-mapped ultrasound image 484 comprise substantially the same anatomical content, and are of the same anatomical region of a same patient, however, the input ultrasound image 482 and the resolution-mapped ultrasound image 484 comprise different appearance characteristics (that is, different resolution profiles). Trained resolution mapping network 486 comprises a learned map from the first resolution domain to a target resolution domain.

Figure 5:
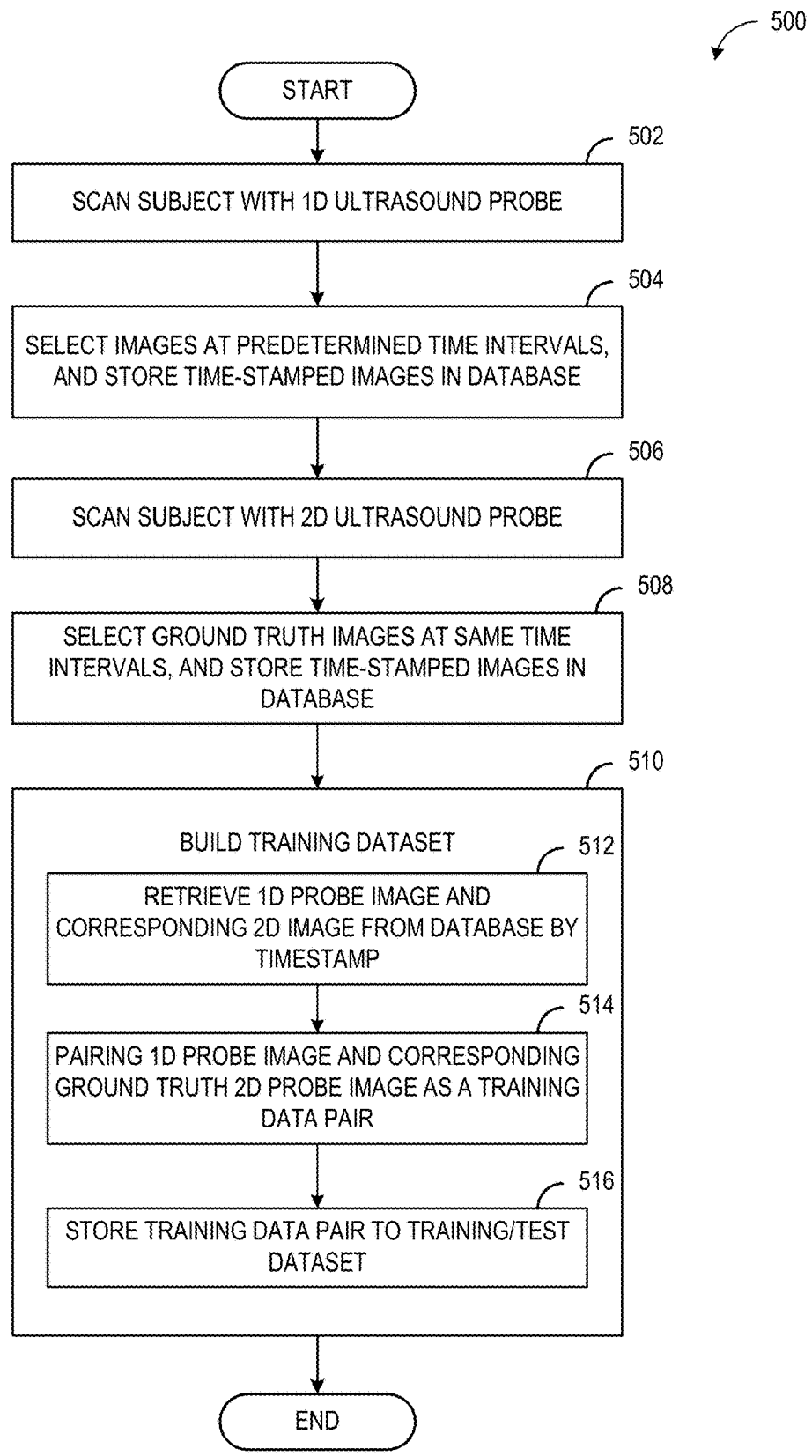
FIG. 5 shows a flowchart of an exemplary method for preparing a training/test dataset for the resolution mapping network training system of FIG. 3.

Referring to FIG. 5, a flow chart of a method 500 is shown for generating training data for training a resolution mapping network (such as the resolution mapping network 302 of the resolution mapping network training system 300 of FIG. 3 and/or the CNN 400 of FIG. 4), according to an exemplary embodiment, wherein the training data comprises a set of image pairs. Each image pair of the set of image pairs may comprise an ultrasound image acquired via a 1D ultrasound probe of one or more anatomical features of a subject acquired at a probe position (e.g., an input image), and a corresponding ultrasound image acquired via a 2D ultrasound probe of the one or more anatomical features of the subject acquired at the probe position (e.g., a ground truth image). Method 500 may be implemented as part of the resolution mapping network training system 300 of FIG. 3 and/or the image processing system 202 of FIG. 2, using ultrasound images acquired by the ultrasound imaging system 100 of FIG. 1. In an embodiment, some operations of method 500 may be stored in non-transitory memory and executed by a processor 206, such as non-transitory memory 206 and processor 204 of image processing system 202 of FIG. 2. In some embodiments, the training image pair, and the plurality of training image pairs, may be stored in an ultrasound image dataset in the training module 210 of image processing system 202 of FIG. 2.

The training data may include sample ultrasound images of abnormalities acquired from subjects who may suffer from one or more conditions, as well as sample ultrasound images of healthy tissues and/or acquired from healthy subjects. For example, ultrasound images acquired for training may include images of organs that are enlarged, swollen, and/or otherwise malformed, or images of anatomical features not present in healthy subjects such as tumors, growths, scar tissue, etc. In an embodiment, a procedure may be followed during the preparation of the training data to acquire images from a broad range of subjects with different characteristics (e.g., age, sex, etc.) and/or of varying degrees of health and/or of anatomical structures of varying degrees of normality/abnormality. In other embodiments, a different procedure may be followed during the preparation of the training data to acquire images from a select group of subjects, where the select group of subjects shares one or more characteristics. For example, images may be acquired from women (e.g., uteruses of pregnant women) but not from men, or images may be acquired from a group of subjects above or below a threshold age (e.g., children or babies). It should be appreciated that the examples provided herein are for illustrative purposes and other criteria may be used to generate the training data.

Method 500 begins at 502, where method 500 includes scanning a subject with a 1D ultrasound probe (e.g., the 1D ultrasound probe 312 of the resolution mapping network training system 300 of FIG. 3). Acquiring images with the 1D probe may be performed based a first set of scanning parameters for each anatomical feature or for each set of anatomical features, the first set of scanning parameters including, for example, scan plane, scan frequency, probe position, focus, aperture size, and scan depth.

In one example, method 500 may include scanning a uterus of a pregnant woman, whereby ultrasound images may be acquired by adjusting a position of the 1D ultrasound probe on the abdomen of the pregnant woman. The ultrasound images may show features of the uterus at different depths, where features of the uterus shown at a depth corresponding to the focal point of a lens of the 1D ultrasound probe may be displayed in high resolution, while features of the uterus shown in the near field and/or far field may be displayed in a lower resolution. Scanning the uterus may involve acquiring a target number of ultrasound images (e.g., corresponding to a duration of an ultrasound examination), where the number of ultrasound images corresponds to a total number of image pairs in the training data. In some embodiments, ultrasound images may be acquired at 502 via a plurality of ultrasound examinations, which may be performed on a plurality of subjects and/or anatomical features of a subject, for example, in order to generate a sufficient number of image pairs in the training data.

At 504, method 500 includes, for a plurality of images acquired via the 1D ultrasound probe, selecting images at a predetermined time interval, and storing it in a database where the image may be accessed based on a time stamp of the image. For example, images (e.g., frames) may be selected at one second intervals from a stream of ultrasound images acquired via the 1D ultrasound probe, such that 60 image frames are selected from a one-minute examination. Alternatively, images may be selected at 10 second intervals from a stream of ultrasound images acquired via the 1D ultrasound probe (e.g., if it is desired that there be greater differences between the ultrasound images than the differences between ultrasound images acquired every second), or all image frames from a stream of ultrasound images acquired via the 1D ultrasound probe may be selected (e.g., if a size of the data set is desired to be maximized).

A timestamp may be associated with each selected image corresponding to a time at which each selected image was acquired with respect to an initiation of the examination. As a non-limiting example, an image acquired 10.27 seconds after the initiation of the examination may receive a timestamp of 10.27. In an embodiment, the timestamp may be automatically associated with the image during acquisition by the ultrasound imaging system. In other embodiments, the timestamp may be associated with the images selected at 504 as part of an image processing stage (e.g., by the processor 204 of the image processing system 202 of FIG. 2, and/or by the image processor 320 of the resolution mapping network training system 300 of FIG. 3). The selected image may be stored in a database where it may be accessed during a later operation of method 500. For example, the selected image may be stored in a relational database table where the timestamp of the selected image is stored in a field of a row of the relational database table, and the selected image is stored in another field of the row of the relational database table, such that the selected image may be identified and retrieved from the database, based on the timestamp of the selected image, by a processor (e.g., the processor 204 of the image processing system 202 of FIG. 2) during an assembling of training image pairs.

At 506, method 500 includes scanning the subject scanned at 502 with a 2D ultrasound probe. A second set of scanning parameters for image acquisition with the 2D probe may correspond to the first set of scanning parameters used with the 1D probe. Specifically, for each anatomical feature or each set of anatomical features scanned with the 1D probe, corresponding images may be acquired with the 2D probe. The corresponding images acquired via the 2D probe may be acquired with the second set of scanning parameters whose values are highly-correlated with values of the first set of scanning parameters used for obtaining the images acquired via the 1D probe. For example, during scanning with the 2D probe, for each anatomical feature, the second of scanning parameters including probe position, scan frequency, scan depth, and scan plane may be adjusted to match the first set of scanning parameters that were used for acquisition with the 1D probe As an example, if a uterus of a pregnant woman is scanned at 502, method 500 may include scanning the uterus of the pregnant woman with a 2-D ultrasound probe at 506, whereby ultrasound images may be acquired by adjusting a position of the 2D ultrasound probe on the abdomen of the pregnant woman. Further, the position of the 2D ultrasound probe on the abdomen of the pregnant woman may be the same as or substantially similar to the position of the 1D ultrasound probe on the abdomen of the pregnant woman used to scan the subject at 502. In an embodiment, as described above in reference to FIG. 3, a position of the 1D ultrasound probe during a first examination may be adjusted in order to acquire an ultrasound image via a mechanized, repeatable automatic process that may be reproduced during a second examination of the abdomen of the pregnant woman with the 2D ultrasound probe. For example, the position of the 1D ultrasound probe during a scanning of the subject at 502 and the position of the 2-D ultrasound probe during a scanning of the subject at 506 may be adjusted via a device that may include a mechanical arm, whereby the position of the 2D ultrasound probe during a scanning of the subject at 506 may be adjusted to the position of the 1D ultrasound probe during a scanning of the subject at 502.

The ultrasound images acquired via the 2D probe may show features of the uterus at different depths, where in contrast to the images acquired by the 1D ultrasound probe, features of the uterus shown at different depths may be displayed in similar high resolution, for reasons described hereinabove. Scanning the uterus at 506 may involve acquiring a target number of ultrasound images (e.g., corresponding to a duration of an ultrasound examination), where the target number of ultrasound images corresponds to the target number of ultrasound images acquired at 502 (e.g., the total number of image pairs in the training data).

As described above in relation to 502, ultrasound images may be acquired at 506 via a plurality of ultrasound examinations performed on a plurality of subjects and/or anatomical features of a subject, where the number of ultrasound examinations performed, the number of subjects, and/or the number of the anatomical features of the subject correspond to the number of ultrasound examinations performed, the number of subjects, and/or the number of the anatomical features of the subject during the acquisition of 1D ultrasound images at 502 on a one-to-one basis. As a result, a high degree of correlation may be established between an input image (e.g., an input image to be used in training a resolution-mapping network) acquired during the first examination via the 1D probe, after a fixed time interval after initiation of the first examination, and a corresponding target image (e.g., a target image to be used in training a resolution-mapping network) acquired during the second examination via the 2D probe, after the same fixed time interval after initiation of the second examination, with respect to a position of the anatomical structure being examined. The input image and the target image can then be paired into a training image pair and added to the training data set.

At 508, method 500 includes, for a plurality of images acquired via the 2D ultrasound probe, selecting images at the predetermined time interval established and used for the selection of 1D probe images (e.g., the input images) at 504, and storing them in the database used for storing the selected 1D probe images, where the images may be accessed based on a time stamp of the images as described above.

At 510, method 500 includes building a training data set. In an embodiment, building a training data set includes, at 512, accessing a 1D probe image and a corresponding 2D probe image from the database, by a reference to a timestamp. For example, an image processor (e.g., the processor 204 of the image processing system 202 of FIG. 2 and/or the image processor 320 of the resolution mapping network training system 300 of FIG. 3) may iteratively retrieve a number of 1D probe images in the database. For each 1D probe image (e.g., input image) retrieved, the processor may select a timestamp of the 1D probe image and use the timestamp to retrieve a 2D probe image (e.g., ground truth image) from the database corresponding to the same subject and anatomical feature as the 1D probe image. At 514, method 500 includes pairing the 1D probe image and corresponding ground truth 2D probe image as a training image pair. At 516, method 500 includes storing the training image pair to a training data set or test data set. As described above in relation to FIG. 3, when an image pair is generated, the image pair may be assigned to either a training set (e.g., the training image pairs 306 of the resolution mapping network training system 300 of FIG. 3) or a test set (e.g., the test image pairs 308 of the resolution mapping network training system 300 of FIG. 3). In an embodiment, the image pair may be assigned to either the training dataset or the test dataset randomly in a pre-established proportion.

As discussed above, generating training and/or testing data sets include, for each subject, acquiring a plurality of scan images acquired via a 1D probe and subsequently acquiring a plurality of corresponding scan images acquired via a 2D probe, and correlating each 1D probe image with its corresponding 2D probe image based on time stamp. In some embodiments, a 1D scan and a corresponding 2D scan may be performed alternatively. For example, a first portion of a body may be scanned with the 1D probe based on 1D scan parameters to obtain a first 1D probe image, and before proceeding to a next portion of the body, the first portion of the body may be scanned with the 2D probe based on 2D scan parameters (probe position, depth, plane, aperture, focus, and frequency) corresponding to 1D probe scan parameters to obtain a first 2D probe image that correspond to the first 1D probe image. The first 1D probe image and the first 2D probe image comprise a first image pair that may be use for training or validation. In this way, a plurality of image pairs (training or validation) may be generated. As an example, a robotic arm may be fitted with the 1D probe and may initiate a 1D scan to obtain a 1D probe image, the 1D scan starting at a first position and ending at a second position on a body to scan an anatomical feature or a set of features or a portion of an anatomical feature. Upon acquiring the image with the 1D probe, the robotic arm may be reset to the first position and re-fitted with the 2D probe. In some examples, the probe used for 1D scanning may be changed to a 2D mode. For example, the ultrasound probe (alternatively referred to herein as ultrasound transducer or as transducer) may be a 2D matrix array probe, and the 1D probe image may be obtained by using a linear array or a first number of rows of the 2D matrix array probe, and the 2D probe image may be obtained by using a second number of rows of the 2D matrix array, where the first number of rows is less than the second number of rows. A 2D scan may be performed to obtain an image from the first position to the second position based on the same scanning parameters (probe position, depth, plane, aperture, focus, and frequency) used for the 1D scan. The 1D probe image and the 2D probe image so obtained may be utilized as a training pair or a validation pair.

Referring to FIG. 6, a flow chart of a method 600 for training a resolution mapping network (such as the resolution mapping network 302 of the resolution mapping network training system 300 of FIG. 3 and/or the CNN 400 of FIG. 4) is shown, according to an exemplary embodiment. In an embodiment, the resolution mapping network may be a deep neural network with a plurality of hidden layers. In an embodiment, the resolution mapping network may be a convolutional neural network such as a convolutional auto-encoder network (CAE). It should be appreciated that the examples provided herein are for illustrative purposes and that any type of neural network may be used by method 600 without departing from the scope of this disclosure.

The training data used in method 600 may include a set of image pairs comprising a 1D ultrasound image of one or more anatomical features of a subject acquired at a probe position (e.g., an input image), and a corresponding 2D ultrasound image of the one or more anatomical features of the subject acquired at the probe position (e.g., a ground truth image), selected and stored in accordance with the procedure described above in reference to method 500 of FIG. 5. Method 600 may be implemented as part of the resolution mapping network training system 300 of FIG. 3 and/or the image processing system 202 of FIG. 2. In an embodiment, one or more operations of method 600 may be stored in non-transitory memory and executed by a processor, such as the non-transitory memory 206 and processor 204 of image processing system 202 of FIG. 2.

Method 600 begins at operation 602, where method 600 includes receiving a training image pair (e.g., comprising an input image acquired via a 1D ultrasound probe and a ground truth image acquired via a 2D ultrasound probe) from a training set. In an embodiment, the training set may be stored in a training module of an image processing system, such as the training module 210 of image processing system 202 of FIG. 2. In other embodiments, the training image pair may be acquired via communicative coupling between the image processing system and an external storage device, such as via an Internet connection to a remote server.

At 604, method 600 includes inputting the input image acquired via the 1D ultrasound probe of the training image pair into an input layer of the resolution mapping network. In some embodiments, the input image is input into an input layer of a CNN, such as CNN 400 of FIG. 4. In some embodiments, each pixel intensity value of the input image may input into a distinct neuron of the input layer of the resolution mapping network.

At 606, method 600 includes receiving an output image from the resolution mapping network. The resolution mapping network maps the input image to an output image by propagating the input image from the input layer, through one or more hidden layers, until reaching an output layer of the resolution mapping network. In some embodiments, the output of the resolution mapping network comprises a 2D matrix of values, wherein each value corresponds to a distinct intensity of a pixel of the input image, and wherein a distinct intensity of each pixel of the output image generates a reconstruction of the input image where a resolution of one or more regions of the output image exceed the resolution of the one or more regions of the input image.

At operation 608, method 600 includes calculating a difference between the output image of the resolution mapping network and the target image of the training image pair. For example, the difference between the output image of the resolution mapping network and the target image of the training image pair (e.g. the ground truth image) may be calculated by determining a difference between the intensity of each pixel of the output image and the intensity of each corresponding pixel in the target image, and summing the differences over all of the pixels of the output image and the target image.

At operation 610, the weights and biases of the resolution mapping network are adjusted based on the difference between the output image and the ground truth image from the relevant data pair. The difference (or loss), as determined by the loss function, may be back-propagated through the neural learning network to update the weights (and biases) of the convolutional layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the resolution mapping network is then updated by adding the negative of the product of the gradient determined (or approximated) for the weight (or bias) with a predetermined step size. Method 600 may then end. It will be noted that method 600 may be repeated until the weights and biases of the resolution mapping network converge, or the rate of change of the weights and/or biases of the deep neural network for each iteration of method 600 are under a threshold.

While not described in method 600, it should be appreciated that in order to avoid overfitting, training of the resolution mapping network may be periodically interrupted to validate a performance of the resolution mapping network on a test set comprising test image pairs. The test image pairs may be generated as described in method 500 of FIG. 5, and may be taken at random from a larger training data set. In an embodiment, training of the resolution mapping network may end when the performance of the resolution mapping network on the test set of image pairs converges (e.g., when an error rate on the test set converges on a minimum value). In this way, method 600 enables a resolution mapping network to be trained to generate a reconstruction of an input image, where the reconstruction of the input image includes more regions of high-resolution and/or consistent high-resolution throughout the reconstructed image.

Figure 7:
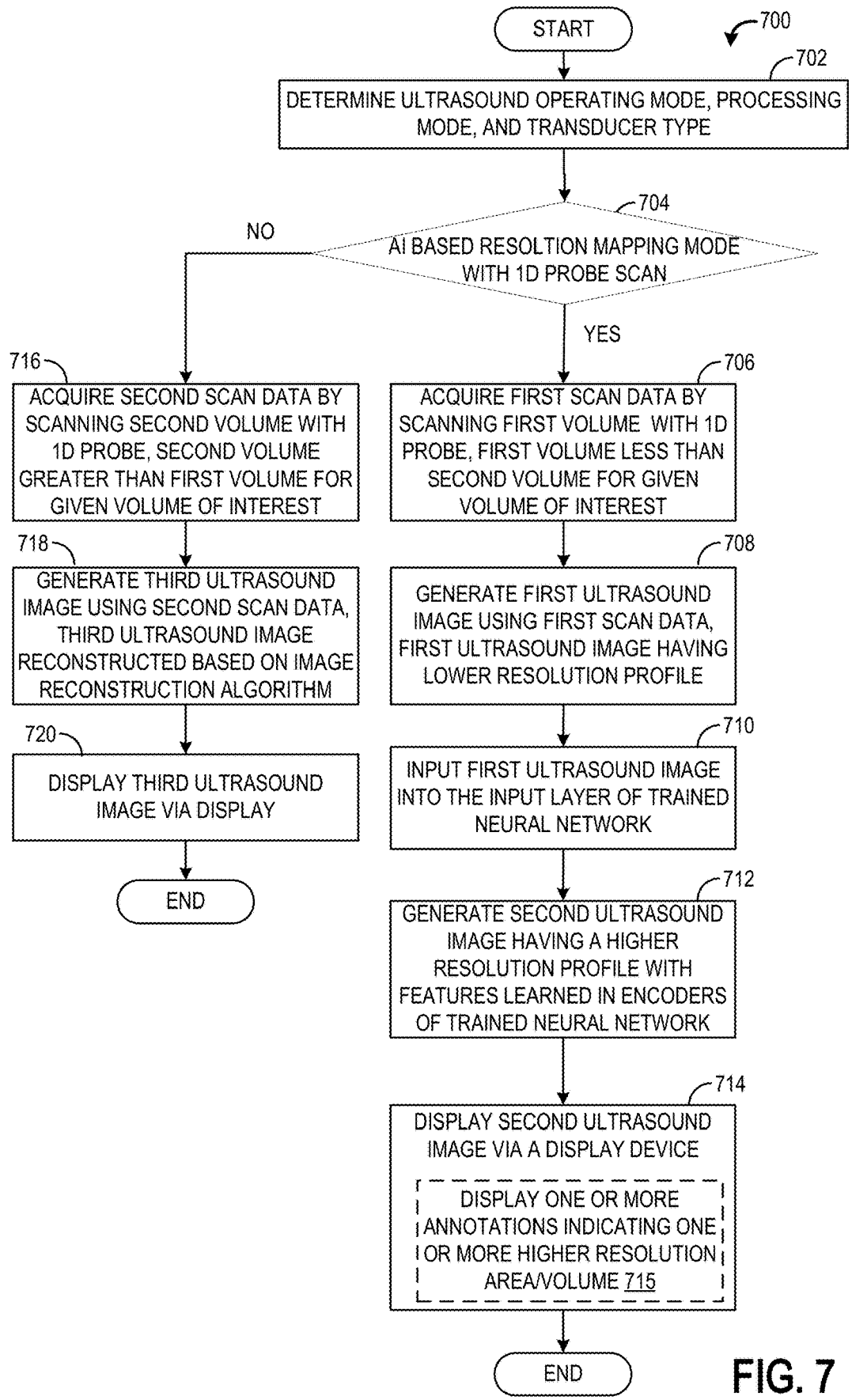
FIG. 7 shows a flowchart of an exemplary method for applying a trained resolution mapping network to map ultrasound images with a first resolution profile to ultrasound images with a second resolution profile.

Referring now to FIG. 7, a flow chart of a method 700 for generating an ultrasound image using an ultrasound imaging system, such as ultrasound system at FIG. 1. The ultrasound imaging system may include a processor, such as the image processing system 202 at FIG. 2. During an operating mode of the ultrasound imaging system, a resolution mapping network (such as the resolution mapping network 302 of the resolution mapping network training system 300 of FIG. 3 and/or the CNN 400 of FIG. 4) may be deployed to generate the ultrasound image, where the ultrasound image has a higher resolution profile as discussed below. In an embodiment, the resolution mapping network may be a deep neural network with a plurality of hidden layers, such as a convolutional neural network, that is trained on a training dataset (generation of training data set is described with respect to FIG. 5) in accordance with the procedure described in method 600 of FIG. 6. Method 700 may be implemented as part of the resolution mapping network training system 300 of FIG. 3 and/or the image processing system 202 of FIG. 2. In an embodiment, one or more operations of method 700 may be stored as executable instructions in non-transitory memory (e.g., non-transitory memory 206 at FIG. 2) and executed by the processor. Further, method 700 may be deployed as part of an inference module such as the inference module 212 of image processing system 202 of FIG. 2, and/or the inference module 322 of the resolution mapping network training system 300 of FIG. 3.

Method 700 begins at operation 702, where method 700 includes determining an operating mode, a processing mode, and a type of transducer used during a scanning operation with the ultrasound system. The operating mode may be a B-mode, M-mode, Doppler mode, Color M-mode, spectral Doppler, Elastography, TVI, strain, or strain rate, etc. The processing mode may be an artificial intelligence based image processing mode that deploys a neural network algorithm, such as trained resolution mapping algorithm 486 at FIG. 4B. The type of transducer may be a 1D transducer, which may be any of a linear array or curved array transducer, or a phased array, a 1.25D transducer, a 1.5D transducer, or a 2D transducer. In one example, the processor may determine the operating mode, the processing mode, and the type of transducer based on user input via an ultrasound imaging interface on a display portion of a display coupled to the ultrasound system.

Next, method 700 proceeds to 704. At 704, method 700 includes determining if the ultrasound scanning is operated in the AI based image processing mode with scan data acquired from a 1D transducer. If the answer at 704 is YES, method 700 proceeds to 706.

At 706, method 700 includes acquiring first scan data with the 1D transducer, wherein the first scan data is obtained by scanning a first volume of a given volume of interest. As a non-limiting example, an operator may scan a first number of parallel image planes with the 1D probe so as to obtain first scan data of the first volume. In one embodiment, the number of image planes may be one. In another embodiment, the number of image planes may be more than one but less than a number of image planes when the AI based resolution mapping mode is not implemented. In particular, the first volume is less than a second volume that may be scanned when the AI based resolution mapping mode is not deployed. As a result, an amount of first scan data obtained when the AI based resolution mapping mode is utilized is less than an amount of second scan data that is obtained when the AI based resolution mapping mode is not utilized. For example, when AI based resolution mapping mode is not deployed, an operator may scan a greater volume and process the greater scan data (that is, the second scan data) in order to generate a 2D image with a higher elevation resolution profile. Said another way, a 1D transducer array may acquire a plurality of 2D cross-sectional images by sweeping across a volume of interest in an elevation direction. Depending on rendering mode (2D or 3D, which may be based on user selection), 2D images with higher elevation resolution or 3D images may be reconstructed from the plurality of 2D cross-sectional images. However, such volumetric scanning with the 1D transducer to achieve desired resolution in elevation direction requires greater skill and experience, which may be challenging for a relatively novice operator, and even when operated by a highly experienced, may not be accurately reproducible. Further, volumetric scan data is processed by an image processing algorithm that is employed (e.g., a Delay-Multiply-and-Sum (DMAS) image reconstruction algorithm, image frame correlation or decorrelation algorithms, etc.) to generate higher resolution 2D image has its own drawbacks such as image artifacts, distortion, lack of dimensional accuracy, etc. Further still, adding mechanical controls to adjust elevation movement of the probe increases bulkiness and complexity of handling, while free-hand scanning lacks reproducibility (with or without experience and skill). In some examples, the reconstruction algorithm may be a neural network based algorithm, which may still require greater volume to be scanned, and may require a greater number of parallel image planes to be scanned with the 1D probe to obtained a desired elevation resolution. Thus, such neural network based algorithms still suffer from problems of lack of dimensional accuracy, reproducibility, complexity of generating scan images, and bulkiness and cost of the transducer (when mechanical controls are added).

In order to improve resolution of the 2D image with scan data obtained from a 1D transducer, such as higher resolution in an elevation direction, and with reduced complexity of scanning and without bulkiness of additional mechanical controls, a trained resolution mapping algorithm may be deployed, as discussed below. Briefly, in the AI based resolution mapping mode, a first volume of a given volume of interest may be scanned with the 1D transducer, where the first volume is less than the second volume that is required when reconstructing plurality of 2D cross sectional images as discussed above. The scan data is then used to generate a first ultrasound image with a lower resolution profile. The first ultrasound sound image is fed into the trained resolution mapping neural network algorithm to obtain a second ultrasound image with a higher resolution profile. In this way, for a given volume of interest, in order to obtain a desired resolution profile, a first volume scanned with the 1D transducer (and hence, first amount of first scan data) is less when AI based resolution mapping is deployed compared to a second volume scanned with the 1D probe (and hence, second amount of second scan data) when AI based resolution is not employed.

Returning to 706, upon scanning the first volume with 1D probe to obtain the first scan data, method 700 proceeds to 708. At 708, method 700 includes generating a first ultrasound image using the first scan data. The first ultrasound image has a lower resolution profile. The lower resolution profile may have lower resolution in one or more of a lateral, axial, and elevation directions.

Next, method 700 proceeds to 710 at which the method includes providing, as input to the trained resolution mapping algorithm, the first ultrasound image with a lower resolution profile. That is, the method includes feeding the first lower resolution image obtained by scanning with the 1D ultrasound probe into an input layer of the trained resolution mapping network.

Next, at 712, method 700 includes generating a second ultrasound image with features learned in one or more encoders of the trained resolution mapping network. The second ultrasound image has a higher resolution profile than the first ultrasound image used as input into the trained resolution mapping algorithm. The higher resolution profile may include a higher resolution in one or more of lateral, axial, and elevation directions.

Upon obtaining the second higher resolution image, at 714, method 700 includes displaying the second higher resolution image via a display portion of a display device (e.g., the display device 234 of image processing system 202 of FIG. 2).

In one embodiment, at 715, the second higher resolution image (that is, the generated image) may include one or more annotations on the generated image to indicate areas that were modified by the neural network to improve resolution. As a non-limiting example, one or more graphical indications, such as outlines of one or more areas on the generated image may be provided so as to enable to user to identify areas that were modified. The user may then make a decision if additional scan with a 2D probe is desired or if the image acquired via the 1D probe and/or the generated image may has desired resolution/clarity for diagnosis. The annotations (that is, graphical indications) may be turned on or off based on user input request, for example.

In some embodiments, the generated image may include annotations including confidence level indications for one or more features whose resolution was improved in the generated image. As a non-limiting example, if a portion of anatomical structure is visible at a first lower resolution in an image acquired via a 1D probe, and after passing the image through the trained neural network algorithm, a generated image is obtained in which the portion of anatomical structure has a second higher resolution and an additional portion of the anatomical structure is indicated in the generated image, a confidence level of the additional portion indicating that the additional portion may be visible when scanned with an actual 2D probe may be indicated on the generated image.

Returning to 704, if the answer is NO, method 700 proceeds to 716. At 716, method 700 includes acquiring second scan data by scanning a second volume of the volume of interest with the 1D probe. In acquiring the second scan data, the 1D probe may scan a second number of parallel image planes in the elevation direction to scan the second volume of interest. The second scan data is greater than the first scan data that is acquired when AI based resolution mapping mode is deployed. During operating conditions when the AI based resolution mapping mode is not deployed, the operator may scan the second volume that is greater than the first volume in order to obtain a second amount of scan data that is greater than the first amount of scan data. Further, a second number of image planes scanned to cover the greater second volume is greater than the first number of images scanned when AI based resolution mapping mode is implemented. Thus in order to obtain to a desired elevation resolution, a greater amount of scan data is required and a greater volume may be scanned with the 1D probe during operating conditions when the AI based resolution mapping network is not deployed.

Upon acquiring the second scan data, method 700 proceeds to 718. At 718, method 700 includes generating a third ultrasound image using second scan data, where the third ultrasound image is reconstructed based on an image reconstruction algorithm. Example image reconstruction algorithms include delay and sum (DAS) beamforming algorithm, Delay-Multiply-and-Sum (DMAS) image reconstruction algorithm, image frame correlation or decorrelation algorithms, pixel-nearest neighbor (PNN), voxel-nearest neighbor (VNN), etc. It will be appreciated that other image reconstruction algorithms may be used; however scan data acquired for image reconstruction when AI based resolution mapping is not deployed may be greater than scan data acquired during operating conditions when AI based resolution mapping is deployed.

A technical effect of generating a data set with image pairs, each image pair including a lower resolution image and a corresponding higher resolution image, training, validating, and testing a neural network based algorithm with the data set for resolution mapping, and deploying the trained resolution mapped algorithm during ultrasound scanning is reduced scan data for acquisition to achieve higher resolution profile. Another technical effect of training and deploying the resolution mapped algorithm is improved resolution profile, particularly in elevation direction. Another technical effect of training and deploying the resolution mapped algorithm is image quality improvement without the use of highly complex control components used for 2D probes. Further, by enabling 1D probe elevation-wise high-resolution, users may obtain meaningful image quality improvement with 1D transducers without any additional hardware upgrade. Further still, novice users may generate high quality, high resolution images since the complexity of scanning and bulkiness of the probe is reduced with the deployment of the resolution mapped algorithm.

An embodiment of a method includes acquiring a first ultrasound image having a first resolution profile; inputting the first ultrasound image to a trained neural network algorithm; generating a second ultrasound image having a second higher resolution profile as an output of the trained neural network algorithm; and displaying the generated second ultrasound image. In a first example of the method, the second higher resolution profile has higher resolution than the first ultrasound image in one or more of an axial direction, a lateral direction, and an elevation direction. In a second example of the method, which optionally includes the first example, the first ultrasound image is acquired with a linear array ultrasound probe or a single row array of a multi-row array probe. In a third example of the method, which optionally includes one or more of the first and second examples, the trained neural network algorithm is trained with a training data set comprising a plurality of image pairs, wherein each of the plurality of image pairs include a first training image and a second training image, the first training image having a lower resolution in one or more of an axial, a lateral, and an elevation direction than the second training image. In a fourth example of the method, which optionally includes one or more of each of the first through third examples, the first training image is obtained via a linear array ultrasound probe and the second training image is obtained via a two-dimensional array ultrasound probe. In a fifth example of the method, which optionally includes one or more or each of the first through fourth examples, the first training image is acquired via first number of rows of a multi-array probe and the second training image acquired via a second number of rows of the multi-array probe, the first number of rows less than the second number of rows. In a sixth example of the method, which optionally includes one or more or each of the first through fifth examples, the first training image and the second training image are obtained with a same set of scan parameters, the scan parameters including a scan depth, a probe position, a scan frequency, a scan aperture, a focus, and a scan plane. In a seventh example of the method, which optionally includes one or more of each of the first through sixth examples, the trained neural network algorithm is trained to extract one or more high resolution features in one or more of the lateral, axial, and elevation directions from the second training image to corresponding low resolution features in the first training image. In an eighth example of the method, which optionally includes one or more of each of the first through seventh examples, the trained neural network algorithm has an autoencoder architecture. In a ninth example of the method, which optionally includes one or more of each of the first through eighth examples, the trained neural network algorithm has a U-Net architecture.

An embodiment of a method includes training a deep learning model to output a higher resolution medical image using, as input, an acquired lower resolution medical image obtained from a medical imaging device, wherein the deep learning model is trained with a training data set comprising a plurality of medical image pairs for each of a plurality of anatomical regions; and wherein each image pair of the plurality of medical image pairs includes a first lower resolution image of a selected anatomical region and a second higher resolution image of the selected anatomical region; and wherein the first lower resolution image and the second higher resolution image are obtained using a same set of scanning parameters, the same set of scanning parameters including a scan plane, a scan frequency, a probe position with respect to a reference marker, a scan aperture, a focus, and a scan depth. In a first example of the method, the first lower resolution image is acquired via a one dimensional ultrasound probe and the second higher resolution image is obtained via a two dimensional ultrasound probe. In a second example of the method, which optionally includes the first example, the first lower resolution image is acquired via first number of rows of a multi-array probe and the second higher resolution image is acquired via a second number of rows of the multi-array probe, the first number of rows less than the second number of rows. In a third example of the method, which optionally includes one or more of the first and second examples, the first number of rows is equal to one, and the second number of rows is greater than one. In a fourth example of the method, which optionally includes one or more of the first through third examples, the deep learning model has an autoencoder architecture or a U-Net architecture. In a fifth example of the method, which optionally includes one or more of the first through fourth examples, the deep learning model is modelled as a generative adversarial network. In a sixth example of the method, which optionally includes one or more of the first through fifth examples, training the deep learning model includes extracting one or more features corresponding to an elevation-wise resolution from the second higher resolution image and applying the one or more extracted features to the lower resolution image to generate a reconstructed higher resolution image.

An embodiment of a system includes an image processing system comprising a display device, a user input device, a trained resolution mapping network, and a processor communicably coupled to the display device, the user input device, and a non-transitory memory storing the trained resolution mapping network and including instructions that when executed cause the processor to receive an ultrasound image of an anatomical region of a subject, the ultrasound image having a first resolution; generate a resolution mapped ultrasound image using the trained resolution mapping network, the resolution mapped ultrasound image having a second resolution greater than the first resolution; and display the resolution mapped ultrasound image via the display device; and wherein the trained resolution mapping network has a convoluted neural network architecture. In a first example of the system, the ultrasound image is acquired with a linear array of an ultrasound probe of an ultrasound imaging device communicatively coupled to the image processing system, and wherein the resolution mapped ultrasound image is generated based on the acquired ultrasound image. In a second example of the system, which optionally includes the first example, the trained resolution mapping network is trained with a first training set and/or a second training set, wherein the first training set comprises a plurality of ultrasound image pairs for each of a plurality of anatomical portions of a human body, each of the plurality of ultrasound image pairs including a first image of an anatomical region obtained from a linear array ultrasound probe and a second image of the anatomical region obtained from a multi-array ultrasound probe; and wherein the second training set comprises another plurality of ultrasound image pairs for each of the plurality of anatomical portions, each of the another plurality of ultrasound image pairs including a third image of the anatomical region obtained from a first number of rows of a multi-array ultrasound probe and a fourth image of the anatomical region obtained from second number of rows of the multi-array ultrasound probe, the first number of rows less than the second number of rows.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
    acquiring a first ultrasound image having a first resolution profile including areas of higher resolution at a single depth;
    building a training data set for training a neural network algorithm, wherein building the training data set includes:
        accessing a plurality of one-dimensional (1D) probe images and a plurality of corresponding two-dimensional (2D) probe images from a database;
        pairing each of the plurality of 1D probe images and each corresponding 2D probe image as a training image pair; and
        storing each training image pair to the training data set;
    inputting the first ultrasound image to the trained neural network algorithm;
    generating a second ultrasound image having a second higher resolution profile as an output of the trained neural network algorithm, the second, higher resolution profile including areas of higher resolution at a plurality of depths; and
    displaying the generated second ultrasound image.

2. The method of claim 1, wherein the first ultrasound image is acquired with a linear array ultrasound probe or a single row array of a multi-row array probe.

3. The method of claim 2, wherein the first training image has a first resolution profile including areas of higher resolution at a single depth, and the second training image has a second, higher resolution profile including areas of higher resolution at a plurality of depths.

4. The method of claim 3, wherein the first training image is obtained via a linear array ultrasound probe and the second training image is obtained via a two-dimensional array ultrasound probe.

5. The method of claim 3, wherein the first training image is acquired via first number of rows of a multi-array probe and the second training image acquired via a second number of rows of the multi-array probe, the first number of rows less than the second number of rows.

6. The method of claim 3, wherein the first training image and the second training image are obtained with a same set of scan parameters, the scan parameters including a scan depth, a probe position, a scan frequency, a scan aperture, a focus, and a scan plane.

7. The method of claim 3, wherein the trained neural network algorithm is trained to extract one or more high resolution features in one or more of the lateral, axial, and elevation directions from the second training image to corresponding low resolution features in the first training image.

8. The method of claim 1, wherein the trained neural network algorithm is trained with a training data set comprising a plurality of image pairs, wherein each of the plurality of image pairs include a first training image and a second training image, the first training image having a lower resolution in one or more of an axial, a lateral, and an elevation direction than the second training image.

9. The method of claim 1, wherein the trained neural network algorithm has an autoencoder architecture.

10. The method of claim 1, wherein the trained neural network algorithm has a U-Net architecture.

11. The method of claim 1, further comprising calculating a difference between an output image and a target image for each training image pair.

12. The method of claim 11, wherein calculating the difference between the output image and the target image for each training image pair includes:
    determining a difference between an intensity of each pixel of the output image and an intensity of each corresponding pixel in the target image; and
    summing the differences over all of the pixels of the output image and the target image.

13. A method, comprising:
    training a deep learning model to output a higher resolution medical image using, as input, an acquired lower resolution medical image obtained from a medical imaging device; and
    building a training data set for training the deep learning model, wherein building the training data set includes:
        accessing a plurality of one-dimensional (1D) probe images and a plurality of corresponding two-dimensional (2D) probe images from a database;
        pairing each of the plurality of 1D probe images and each corresponding 2D probe image as a training image pair; and
        storing each training image pair to the training data set,
    wherein the deep learning model is trained with the training data set, the training data set comprising a plurality of medical image pairs for each of a plurality of anatomical regions;
    wherein each image pair of the plurality of medical image pairs includes a first lower resolution image of a selected anatomical region, the first, lower resolution image including areas of higher resolution at a single depth; and a second higher resolution image of the selected anatomical region, the second, higher resolution profile including areas of higher resolution at a plurality of depths; and wherein the first lower resolution image and the second higher resolution image are obtained using a same set of scanning parameters, the same set of scanning parameters including a scan plane, a scan frequency, a probe position with respect to a reference marker, an aperture size, a focus, and a scan depth.

14. The method of claim 13, wherein the first lower resolution image is acquired via a one dimensional ultrasound probe and the second higher resolution image is obtained via a two dimensional ultrasound probe.

15. The method of claim 13, wherein the first lower resolution image is acquired via first number of rows of a multi-array probe and the second higher resolution image is acquired via a second number of rows of the multi-array probe, the first number of rows less than the second number of rows.

16. The method of claim 15, wherein the first number of rows is equal to one, and the second number of rows is greater than one.

17. The method of claim 13, wherein the deep learning model has an autoencoder architecture or a U-Net architecture.

18. The method of claim 13, wherein the deep learning model is modelled as a generative adversarial network.

19. The method of claim 13, wherein training the deep learning model includes extracting one or more features corresponding to an elevation-wise resolution from the second higher resolution image and applying the one or more extracted features to the lower resolution image to generate a reconstructed higher resolution image.

20. An image processing system, comprising:
a display device;
a user input device;
a trained resolution mapping network, the trained resolution mapping network trained on a training data set including training image pairs, each training image pair including a first training image including areas of higher resolution at a single depth, and a second, target training image including areas of higher resolution at a plurality of depths, wherein the training data set is built based on a plurality of one-dimensional (1D) probe images and a plurality of corresponding two-dimensional (2D) probe images accessed from a database, and wherein each of the plurality of 1D probe images and each corresponding 2D probe image are paired as a training image pair; and
a processor communicably coupled to the display device, the user input device, and a non-transitory memory storing the trained resolution mapping network and including instructions that when executed cause the processor to:
receive an ultrasound image of an anatomical region of a subject, the ultrasound image having a first resolution;
generate a resolution mapped ultrasound image using the trained resolution mapping network, the resolution mapped ultrasound image having a second resolution greater than the first resolution; and
display the resolution mapped ultrasound image via the display device; and wherein the trained resolution mapping network has a convoluted neural network architecture.

21. The image processing system of claim 20, wherein the ultrasound image is acquired with a linear array of an ultrasound probe of an ultrasound imaging device communicatively coupled to the image processing system, and wherein the resolution mapped ultrasound image is generated based on the acquired ultrasound image.

22. The image processing system of claim 20, wherein the trained resolution mapping network is trained with a first training set and/or a second training set; wherein the first training set comprises a plurality of ultrasound image pairs for each of a plurality of anatomical portions of a human body, each of the plurality of ultrasound image pairs including a first image of an anatomical region obtained from a linear array ultrasound probe and a second image of the anatomical region obtained from a multi-array ultrasound probe; and wherein the second training set comprises another plurality of ultrasound image pairs for each of the plurality of anatomical portions, each of the another plurality of ultrasound image pairs including a third image of the anatomical region obtained from a first number of rows of a multi-array ultrasound probe and a fourth image of the anatomical region obtained from second number of rows of the multi-array ultrasound probe, the first number of rows less than the second number of rows.

23. The image processing system of claim 20, wherein weights and biases of the resolution mapping network are adjusted based on a difference between an output image and a ground truth image from training data pairs.

* * * * *